United States Patent [19]

Pembroke

[11] Patent Number: 4,546,519

[45] Date of Patent: Oct. 15, 1985

[54] APPARATUS FOR CLEANING TUBES

[75] Inventor: Lawrence Pembroke, Brentwood, England

[73] Assignee: Hyprovac (U.K.) Limited, Rayleigh, England

[21] Appl. No.: 602,437

[22] Filed: Apr. 20, 1984

[51] Int. Cl.$^4$ ............................................. B08B 9/02
[52] U.S. Cl. ................................ 15/395; 15/104.3 SN
[58] Field of Search ........ 15/395, 315, 304, 104.3 SN; 134/166 C, 167 C, 168 C, 169 C

[56] References Cited

U.S. PATENT DOCUMENTS

| 1,538,698 | 5/1925 | Hall | 15/104.3 SN |
|---|---|---|---|
| 2,193,999 | 3/1940 | Allen | 15/304 X |
| 2,488,490 | 11/1949 | Buchmiller | 15/104.3 SN |
| 2,718,376 | 9/1955 | Raney | 15/104.3 SN X |
| 3,159,861 | 12/1964 | Sarcone | 15/104.3 SN |
| 3,747,153 | 7/1973 | O'Neill | 15/104.3 SN |
| 4,326,317 | 4/1982 | Smith et al. | 15/395 X |

FOREIGN PATENT DOCUMENTS

| 2064410 | 8/1971 | Fed. Rep. of Germany | 15/387 |
|---|---|---|---|
| 1112107 | 5/1968 | United Kingdom | 15/104.3 SN |

Primary Examiner—Chris K. Moore

[57] ABSTRACT

An apparatus for cleaning tubes which apparatus comprises a hollow barrel which is connected to a primary drum containing a coiled resilient tape so that the tape may pass from the drum along and out of one end of the barrel, an electric motor operatively connected to an inner end of the coil of tape and arranged to rotate the coil of tape and to drive the tape out of the barrel and to retract it into the drum, a cleaning device such as a brush attached to an outer end of the coil of tape, and a vacuum hose connected to the other end of the barrel and adapted for connection to a vacuum generating apparatus to create suction at said one end of the barrel, in which apparatus there is provided associated with the drum and the coil of tape a proximity switch sensor and a plurality of targets adapted to be sensed by the proximity switch sensor, relative rotation between the sensor and the targets causing the sensor to transmit impulses to a visible display device to indicate the amount of tape unwound from the coil.

17 Claims, 1 Drawing Figure

U.S. Patent  Oct. 15, 1985  4,546,519
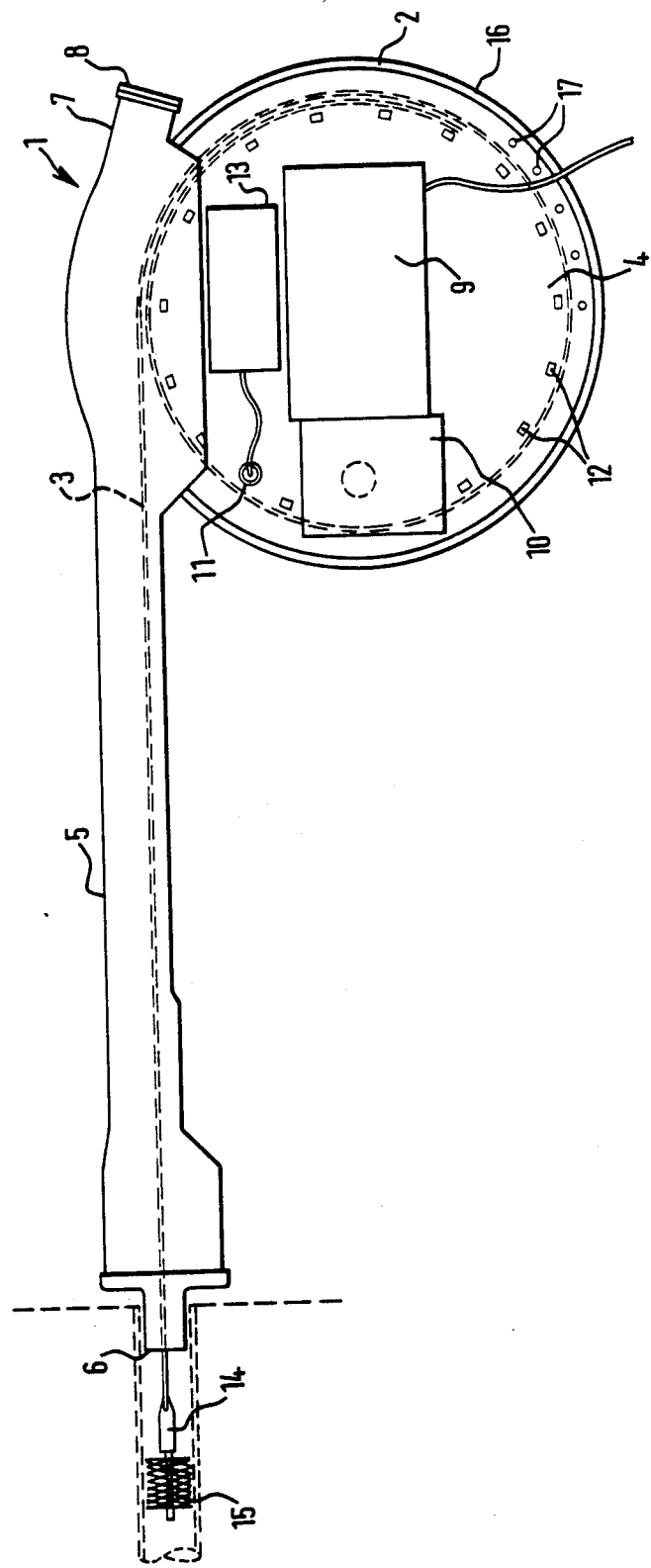

APPARATUS FOR CLEANING TUBES

This invention relates to an apparatus for cleaning the tubes of tubular plant, such as the smoke tubes of boilers.

A known apparatus for this purpose comprises a hollow barrel, a cast metal drum attached thereto, a steel tape coiled within said drum and protruding from the barrel and having a brush or other cleaning attachment mounted at its end, an electric motor for extending the tape from the barrel and for retracting it into the drum, and a vacuum hose connected to the mouth of the barrel for collecting soot, dust and debris dislodged by the brush.

The known apparatus suffers from various disadvantages:

- spring steel tape is expensive and prone to breakage and also is heavy which latter renders a hand held apparatus cumbersome and unwieldy;
- the use of a cast metal drum makes it difficult readily to service and maintain the cleaing and other mechanisms located within the drum, and such a drum is inconviently heavy;
- the location of the vacuum hose at the mouth of the barrel increases the bulk of the barrel and makes the apparatus unwieldy;
- in order to indicate to the operator the amount of tape extending from the drum a mechanical gearing system is employed:- no means however is provided to prevent brush overrun, thereby to prevent damage to the boiler refractories or the tape.

The present invention has as an object the elimination or amelioration of some or all of the defects of such known apparatus.

According to the present invention there is provided an apparatus for cleaning tubes, which apparatus comprises a hollow barrel which is connected to a primary drum containing a coiled resilient tape so that the tape may pass from the drum along and out of one end of the barrel, an electric motor operatively connected to the inner end of the tape and arranged to rotate the coil of tape about the coil axis to drive the tape out of the barrel and to retract the tape into the drum, a cleaning device such as a brush attached to an the outer end of the coil of tape, and a vacuum hose connected to the other end of the barrel and adapted for connection to a vacuum generating apparatus to create suction at said one end of the barrel, in which apparatus there is provided associated with the drum and the coil of tape a proximity switch sensor and a plurality of targets adapted to be sensed by the proximity switch sensor, relative rotation between the sensor and the targets causing the sensor to transmit impulses to a visible display device to indicate the amount of tape unwound from the coil.

By locating the vacuum hose at an end of the barrel opposite from its operative or forward end the bulk of the forward end of the barrel is reduced and the apparatus made less cumbersome and more easily usable.

Preferably the apparatus is adapted for cleaning smoke tube boilers.

The proximity switch sensor and targets enable the hitherto-used mechanical reduction gearing to be dispensed with and provides a light weight and accurate system for indicating the length of tape unwound from the coil and hence of the length of tape extending from the barrel.

Preferably the tape is mounted upon the outer periphery of an inner drum arranged to be driven by the electric motor, which inner drum is provided about its inner periphery with said plurality of targets, the proximity switch being fixedly located relative to the primary drum and preferably being located within the inner drum. In an alternative embodiment, the targets may be embedded at intervals within the tape itself.

The apparatus will include manually operable motor switching means for causing the motor to extend and retract the tape. Preferably the visible display device includes means for pre-setting a maximum value for the extension of the tape and comparator means for comparing the actual value of tape extension with the preset value and for preventing further extension of the tape when the said actual value equals or exceeds said preset value. Preferably said comparator means also prevents retraction of the tape beyond a predetermined minimum value for tape extension.

An important preferred feature of the apparatus of the present invention is that the tape be made, not of spring steel but of a synthetic material possessing longitudinal rigidity, resilience and low weight. Such a material may be a thermoplastics material which may be reinforced e.g. with longitudinally extending strands of steel wire, glass fibre or carbon fibre but is preferably a composite of a thermosetting resin, glass fibre and carbon fibre.

The primary drum of the apparatus, hitherto made of cast metal, may be a moulding of a thermoplastics polymer, glass reinforced plastics or of a structural foam material. Generally, roller bearings are provided about the inner periphery of the primary drum to reduce friction between the tape and the drum. It has been found that such bearings can require replacement or maintenance and this has hitherto required considerable disassembly of the apparatus. According to a preferred feature of the invention the primary drum comprises a pair of substantially concentric generally disc shaped members and a removable resilient strip secured about and extending between the peripheries of said members. The resilient strip is preferably composed of an elastomeric material such as P.V.C, rubber or neoprene to facilitate its removal and refitting and additionally to provide a degree of shock-absorption if the apparatus is accidentally dropped.

An embodiment of the present invention will now be described, by way of example only, by reference to the accompanying drawing, in which:

The single FIGURE is a diagrammatic side elevation of an embodiment of apparatus according to the present invention.

Referring to the drawing, a tube cleaning apparatus 1 comprises a primary drum 2 of glass-reinforced plastics or of a structural foam material. Coiled within the primary drum 2 is a resilient tape 3 of steel wire and glass-reinforced plastics material, mounted for rotation upon an inner drum 4. The tape is approximately 2 mm thick and 8 meters long. A hollow barrel 5 is connected to the primary drum 2 so that the tape 3 may pass from the primary drum 2, along and out of the distal end 6 of the barrel 5. The proximal end 7 of the barrel 5 is provided with connecting means 8 whereby a suction hose (not shown) may be connected to the barrel 5.

An electric motor 9 is provided upon the primary drum 2 arranged to drive the inner drum 4 in rotation via a gear box 10. There is provided within the inner drum 10 is a proximately switch sensor 11 adapted to produce a signal when a target is detected. A plurality of suitable metal targets 12 for detection by said proximity switch sensor 11 is provided about the inner circumference of the inner drum 10 at regularly spaced intervals and the sensor 11 is arranged to transmit said signals to an optical read out and control device 13. Alternatively, these targets 12 may be embedded at intervals along the length of the tape in a manner not shown but which will be readily apparent to those with ordinary skill in the art. The device is calibrated so that as the inner drum 10 rotates and extends or acts in the tape 3 a direct measure of the extent of extension of the tape 3 is displayed. The control device 13 includes means (not shown) for electronically pre-setting a maximum value of tape extension and includes comparator means (not shown) for comparing the actual value of tape extension with the pre-set value and for preventing further extension of the tape 3 when said actual value equals or exceeds said preset value. Additionally the comparator means is adapted to prevent retraction of the tape 3 beyond a predetermined minimum value.

The distal end 14 of the tape 3 is provided with a connector whereby cleaning attachments such as the brush 15 shown may be connected.

The primary drum consists of a pair of generally parallel discs spaced apart by 18 axially extending pins with a removable resilient strip 16 of elastomeric material secured about and extending between the peripheries of said discs. A plurality of roller bearings 17 is provided about the inner periphery of the primary drum, mounted upon said pins, to reduce friction between tape and drum. The removable strip facilitates maintenance of the bearings and inspection of the mechanisms of the apparatus.

It will be appreciated that by means of the present invention the disadvantages of the prior art apparatus can be alleviated or obviated.

The invention includes all such modifications and alternative arrangements such as would be apparent to a person skilled in the art, and the claims hereinafter are to be interpreted in the light of this.

I claim:

1. An apparatus for cleaning tubes comprising a hollow barrel; a primary drum containing a coiled resilient tape; means connecting said drum to said barrel so that said tape may pass from said drum along and out of one end of said barrel; an electric motor operatively connected to the inner end of said tape and arranged to rotate said coil of tape about the axis of said coil to drive said tape out of said barrel and to retract it into said drum; a cleaning device attached to the outer end of said tape; a vacuum hose connected to the other end of said barrel and adapted for connection to a vacuum generating apparatus to create suction at said one end of said barrel, in which apparatus there is provided associated with the drum and the coil of tape a proximity switch sensor; a plurality of targets adapted to be sensed by said proximity switch sensor, said proximity switch sensor and targets being operatively associated with said drum and said coil of tape; and a visible display device connected to said sensor, whereby relative rotation between said sensor and said targets causes said sensor to transmit impulses to said visible display device to indicate the amount of tape unwound from said coil.

2. Apparatus as claimed in claim 1, wherein said proximity switch sensor is fixedly located within the drum and said plurality of targets is arranged to rotate with said coil of tape.

3. Apparatus as claimed in claim 2, wherein said tape is mounted for rotation upon the outer periphery of an inner drum located within said primary drum and said targets are mounted about the inner periphery of said inner drum.

4. Apparatus as claimed in claim 2, wherein said targets are embedded at intervals within said tape.

5. Apparatus as claimed in claim 1, wherein said proximity switch sensor senses changes in electromagnetic induction and said targets are of metal.

6. Apparatus as claimed in claim 1, wherein said tape is composed of a synthetic material possessing longitudinal rigidity, resilience and low weight.

7. Apparatus as claimed in claim 6, wherein said tape is composed of a thermoplastics material.

8. Apparatus as claimed in claim 7, wherein said tape is reinforced by longitudinally extending strands selected from the group consisting of steel wire, glass fibres and carbon fibres.

9. Apparatus as claimed in claim 6, wherein said tape is composed of a glass fibre and carbon-fibre reinforced resin.

10. Apparatus as claimed in claim 1, wherein said primary drum is fabricated from a synthetic resin.

11. Apparatus as claimed in claim 10, wherein said drum is fabricated from a material selected from glass reinforced plastics and structural framed plastics.

12. Apparatus as claimed in claim 10, wherein said primary drum comprises a pair of substantially parallel, concentric, generally disc-shaped members and a removable resilient strip secured about and extending between the peripheries of said disc-shaped members.

13. Apparatus as claimed in claim 12, wherein said strip is composed of an elastromeric material.

14. Apparatus as claimed in claim 1, wherein said visible display device includes means for pre-setting a maximum value for the extension of said the tape and comparator means for comparing the actual value of tape extension indicated by said visible display device with the preset value and for preventing further extension of said tape when the said actual value equals or exceeds said preset value.

15. Apparatus as claimed in claim 14, wherein said comparator means also prevents retraction of said tape beyond a predetermined minimum value for tape extension.

16. An apparatus for cleaning tubes comprising a hollow barrel; a primary drum containing a coiled resilient tape; means connecting said barrel to said drum so that said tape may pass from said drum, along and out of one end of said barrel; an electric motor operatively connected to the inner end of said tape and arranged to rotate said coil about the axis of said coil and to drive said tape out of said barrel and to retract said tape into said drum; a cleaning device attached to the outer end of said coil of tape; a vacuum hose connection on said barrel for placing a vacuum hose in communication with the interior of said barrel, thereby to connect said barrel to a vacuum generating apparatus to create suction at said one end of said barrel, said tape being composed of a composite material comprising a resin matrix and longitudinally extending reinforcing strands of glass fibre and of carbon fibre.

17. Apparatus according to claim 16, wherein said tape is formed by pulling the reinforcing fibres through a curing die after they have been coated with a durable resin thereby to cure and shape said tape.

* * * * *